United States Patent
Jacobsen et al.

[11] Patent Number: 5,980,496
[45] Date of Patent: Nov. 9, 1999

[54] TOPICAL DRUG DISPERSING APPARATUS

[75] Inventors: Stephen C. Jacobsen; Clark Davis, both of Salt Lake City, Utah

[73] Assignee: Sarcos L.C., Salt Lake City, Utah

[21] Appl. No.: 08/988,944

[22] Filed: Dec. 11, 1997

[51] Int. Cl.⁶ .................................................. A61M 35/00
[52] U.S. Cl. .......................... 604/289; 604/290; 604/308; 604/892.1; 119/654; 119/656; 119/606; 119/857; 119/860
[58] Field of Search .............................. 604/20, 131, 151, 604/289, 304, 305, 308; 119/650, 652, 653, 654, 655, 858, 860

[56] References Cited

U.S. PATENT DOCUMENTS

| | | |
|---|---|---|
| 3,840,009 | 10/1974 | Michaels et al. . |
| 4,102,332 | 7/1978 | Gessman . |
| 4,141,359 | 2/1979 | Jacobsen et al. . |
| 4,250,878 | 2/1981 | Jacobsen et al. . |
| 4,312,347 | 1/1982 | Magoon et al. . |
| 4,326,522 | 4/1982 | Guerrero et al. . |
| 4,425,117 | 1/1984 | Hugemann et al. . |
| 4,439,197 | 3/1984 | Honda et al. . |
| 4,457,752 | 7/1984 | Vadasz . |
| 4,562,794 | 1/1986 | Speckman ................................ 119/156 |
| 4,564,363 | 1/1986 | Bagnall et al. . |
| 4,930,451 | 6/1990 | Miller et al. ............................. 119/106 |
| 4,942,883 | 7/1990 | Newman ................................... 128/798 |
| 4,968,297 | 11/1990 | Jacobsen et al. . |
| 5,135,479 | 8/1992 | Sibalis et al. . |
| 5,167,625 | 12/1992 | Jacobsen et al. . |
| 5,196,002 | 3/1993 | Hanover et al. . |
| 5,522,798 | 6/1996 | Johnson et al. . |
| 5,527,288 | 6/1996 | Gross et al. . |
| 5,582,593 | 12/1996 | Hultman . |
| 5,616,132 | 4/1997 | Newman . |
| 5,618,269 | 4/1997 | Jacobsen et al. ........................ 604/118 |
| 5,823,989 | 10/1998 | Ostrow .................................... 604/20 |

*Primary Examiner*—Wynn Wood Coggins
*Assistant Examiner*—Patricia Bianco
*Attorney, Agent, or Firm*—Thorpe North & Western LLP

[57] ABSTRACT

The method for automatic dosing of drugs utilizes a delivery device which may be administered to an animal. The delivery device is configured to have one or more compartments or reservoirs, each containing at least one drug so that a plurality of doses of the drug(s) are held within the device. In accordance with the present invention, the delivery device selectively releases doses of the drug(s) to provide an efficacious dosing pattern. One primary function of the present invention is to release two or more pesticides in such a pattern that parasites are effectively controlled while preventing the development of tolerance to the drugs within the parasites. Preferably, the delivery device is programmable to effectuate the release of the drug(s) at a desired time to maintain efficacious levels of the drug while minimizing the amount of drug which must be used.

20 Claims, 9 Drawing Sheets

TOPICAL DRUG DISPERSING APPARATUS

BACKGROUND OF THE INVENTION

1. Field of the Invention

The present invention relates to an apparatus for automatic dispensing of drugs. More particularly, the present invention relates to an apparatus for an animal which utilizes electromechanical mechanisms for dosing of drugs and a dispenser to ensure that the drug is delivered to the recipient.

2. State of the Art

It is well known in the fields of animal husbandry and veterinary medicine that it is usually desirable and often necessary to treat animals with drugs for parasites. The parasites of concern will often vary depending on the animal concerned and may include both ectoparasites and endoparasites. To eliminate or control these parasites, animals are often sprayed with or fed parasiticides, injected with parasiticide drugs, or provided with collars or other attachable devices that are saturated with a parasiticide. With farm animals, in order to control parasites, the farm animals typically must be rounded up and placed in a holding area so that each animal may be properly dosed with the drug(s). Once treated, the animal is released until the next dosing is required.

Figure 1:
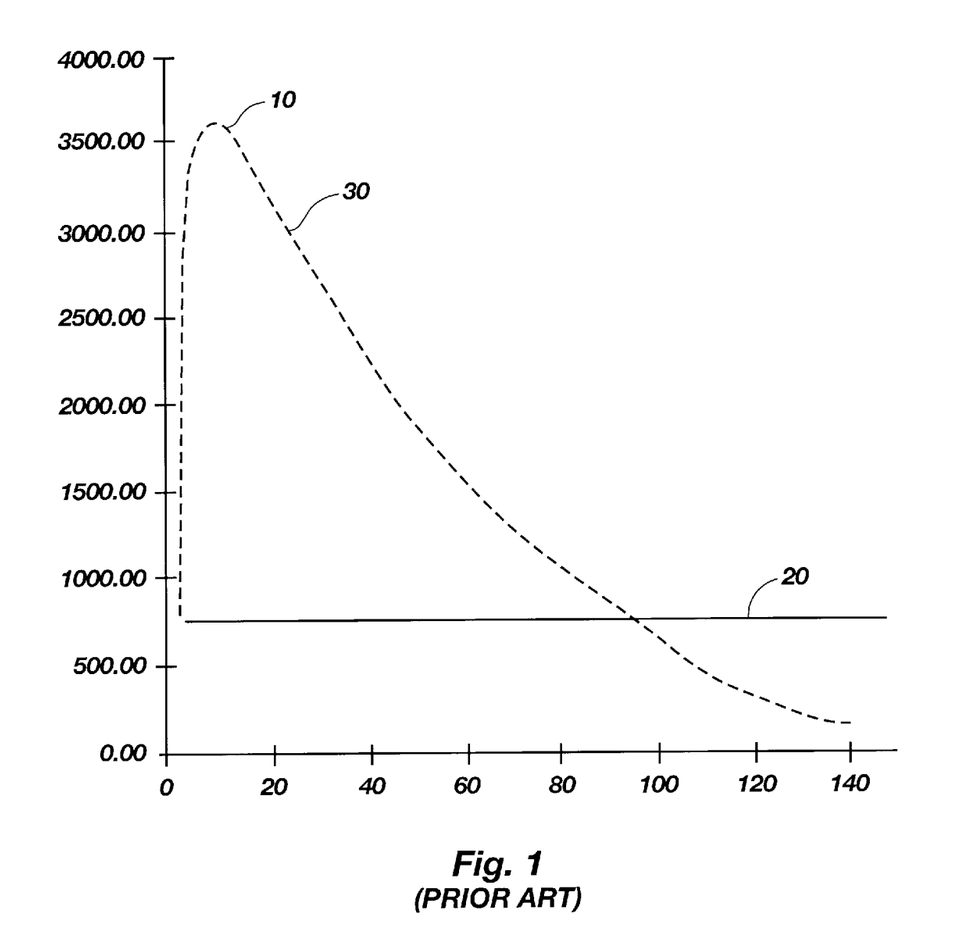
FIG. 1 illustrates a graph demonstrating a first-order kinetic decline of drug levels in/on an animal when the drug is delivered by a device that releases the drug by a conventional diffusion method.

Unfortunately, rounding up the animals each month, etc., is time consuming and expensive. The animal must be located and then brought to a suitable location for administration of the drug. Because of the time and expense involved with such round-ups, the farmer is forced into a compromise of overdosing the animal with a very large dose of the drug to prolong the period during which the drug is present at levels which meet or exceed the minimum effective level, thereby decrease the frequency with which the drugs must be administered, or accepting the expense of frequent round-ups to repetitively doses the animals. For example, a topically applied drug may have an efficacy threshold which relates to a 750 milligram dose of a given medication. However, to extend the period between dosing, a significantly larger dose is typically used. In FIG. 1, there is shown a curve indicating a normal, exponentially declining (i.e., first-order) efficacy curve where the drug is provided by prior art diffusion devices, such as ear tags, at a very high initial dose in order to maintain drug levels above the efficacy threshold for a prolonged period.

Referring to FIG. 1, the initially high drug level 10 that is available early in the treatment period is typically much higher than the efficacy threshold 20. In the present example, the initially high drug level 10, is 3,750 milligrams, a drug level that would require a dose which is at least four to five times higher than the efficacy threshold for the drug used. Such large doses create several problems and negatively impact the animal by causing host toxicity, decreased weight gains, and loss of income to the animal handlers/owners.

An additional problem with the initial high dose is that high levels of the drug may still be present should the farmer desire to slaughter the animal within the time period correlated with the upper portion, indicated at 30, of the first-order declining kinetic curve. The high, persistent drug levels can limit the farmer's marketing response and potentially lead to adverse reactions in consumers.

In the FIG. 1 example, the drug, assumed to be a parasiticide for discussion purposes, which has been diffused onto/into the animal remains above the efficacy threshold for approximately 90 days. Once the amount of drug present falls below the efficacy threshold, the drug is present in insufficient amounts to adequately kill the targeted parasites. However, it is well known that the prolonged presence of subtherapeutic levels of a drug gives rise to the development of resistance to the drug within the targeted parasites. In a resistant parasite population, the efficacy threshold is shifted upward substantially. Therefore, due to use of prior art diffusion controlled dosage forms, numerous previously beneficial antibiotics and parasiticides are now of limited effectiveness because the target microbes and parasites have developed sufficient resistance to the drug to withstand even very high dosages that the host animal cannot tolerate. Drugs that are not biocides also are negatively impacted by this type of dosing pattern as manifested by enzyme down regulation and the clinical development of tachyphylaxis.

There have been numerous attempts to overcome these concerns. For example, it has been proposed to implant in farm animals devices which provide for the release of drugs at a time other than implantation. Examples of such devices are included in the U.S. Pat. Nos. 4,564,363, 4,326,522, 4,425,117, 4,439,197, 3,840,009, 4,312,347 and 4,457,752. Unfortunately, these devices tend to be expensive to use, typically they allow only for a one time (continuous) discharge of a single drug, and are otherwise disadvantageous.

Conventional collars for dogs, cats, and other domestic animals have met with limited success. While they are relatively inexpensive to purchase, they suffer from the same drawbacks as the aforementioned methods of administering parasiticides to farm animals. That is, the collar typically contains a relatively high concentration of the parasiticide when first used. The concentration, however, declines in a first-order declining kinetic curve (similar to that shown in FIG. 1) and thus may have the same drug resistant effect on the targeted parasite. Thus, there is a need for a method of administering drugs to animals which overcomes the disadvantages of the prior art.

SUMMARY OF THE INVENTION

It is an object of the present invention to provide an improved apparatus for dosing animals that comprises a self contained integrated unit.

It is another object of the invention to provide such an apparatus for dosing animals in which one or more drugs are topically adminstered to the animal.

It is yet another object of the invention to provide an apparatus for dosing animals in which one or more topically adminstered drugs are held in a dispenser for a period of time to increase the likelihood that the drug will be contacted by and deposited on the animal.

It is another object of the invention to provide an apparatus that substantially prevents the drug or drugs being topically adminstered onto the animal from running, dripping, or otherwise being dispensed in an excessive manner.

It is another object of the present invention to provide an improved apparatus for dosing animals which requires only a single application to the animal during a treatment period.

It is yet another object of the present invention to provide such an apparatus which prevents or substantially reduces the development of drug resistance within the targeted parasite or microbe.

It is still another object of the present invention to provide an apparatus which maintains an efficacious dose of the drug within the animal throughout the treatment period.

It is yet another object of the present invention to minimize the amount of drug necessary to stay above the drug's efficacy threshold by providing a dispensing device that maintains the drug in contact with the animal until the drug is received by the animal.

It is still yet another object of the present invention to enable the user to control the amount of the drug present in the animal's system to thereby enable the user to increase drug levels during traditionally high periods of parasite infestation.

Yet another object of the present invention is to provide such an apparatus which provides electronic control over drug delivery, rather than depending on the chemical attributes of the drug being delivered.

The above and other objects not specifically enumerated are realized in specific illustrated embodiments of an apparatus for automatic repetitive dosing of a single drug or alternate dosing of two or more drugs including a delivery system which has at least one container or reservoir for holding at least one drug to be dosed and which is attached to the animal. The delivery system is programmed to release an initial dose of the drug to the animal. The initial dose is then followed by periodic doses of the drug to achieve an efficacious treatment of the animal.

In accordance with one aspect of the invention, the doses are administered to the animal through a dispenser attached to a collar or other structure that is secured to the animal. In a preferred embodiment, the dispenser comprises a plurality of concentric ribs projecting from the dispenser defining a plurality of concentric grooves thereinbetween. The drug is dispensed into the center of the dispenser and is held therein by capillary action until the animal makes contact with the dispenser and receives the drug. Thus, the drug is dispensed through the center and travels over ridges to adjacent grooves, increasing likelihood that the drug will be dispensed onto the animal. Accordingly, such a dispenser substantially prevents the drug from dripping or otherwise escaping the confines of the dispenser without being deposited on the animal.

Other configurations of a dispenser may include parallel walls, raised portions in a checkerboard configuration, stipples, nubs, and the like.

It is also contemplated that the dispenser be comprised of a porous pad, such as a sponge or fabric-like material. Such a pad can contain the drug until contact with the animal disperses the drug onto the animal.

After an initial dose of the drug has been dispensed, the drug typically will diminish, for example, in a first-order kinetic decline. Before the drug is allowed to pass below the efficacy threshold which has been established, the drug dispensing apparatus releases a second dose of the drug to maintain the amount of the drug in the animal above the efficacy threshold for the drug.

In yet another aspect of the present invention, the drug dispensing apparatus dispenses a first drug. Before the first drug is allowed to pass below the known efficacy threshold for the first drug, the drug dispensing apparatus releases an initial dose of a second drug which is sufficient to bring the amount of the second drug in/on the animal above the efficacy threshold for the second drug. The dosing of the first and second drugs are then cycled to achieve a desired efficacy by always maintaining at least one of the drugs at levels above the efficacy threshold for that drug. This repetitive dosing approach maintains high-level efficacy with a minimum drug exposure for the host animal and the environment. For example, the first and second drugs may be administered shortly before the other drug drops below the efficacy threshold, or several doses of the first drug may be provided with an occasional dose of the second drug, or several doses only of the first drug may be provided In accordance with another aspect of the present invention, the first and second drugs are delivered in such a manner that each drug remains present in the body in amounts above the efficacy threshold, or, the two drugs may be alternated to ensure that at least one of the drugs is always well above the efficacy threshold without introducing excessive amounts of either drug into the animal.

In accordance with yet another aspect of the present invention, the drug dispensing apparatus could be used to supply a plurality of different drugs with any desired sequence and timing during a designated period. Thus, for example, antibiotics or parasiticides could be delivered monthly as described above and other drugs, such as hormones which stimulate animal growth, could also be provided. The use of the dispensing apparatus allows a farmer to provide all of the medication needs for an animal for a prolonged period of time with a single administration of the programmed microdelivery system. Such a method can save considerable amounts of time and money by avoiding repetitive handling of the animals, avoiding doses which may induce toxicity in the host, and maximizing efficacy with minimal drug doses.

In accordance with still another aspect of the present invention, the amount of drug delivered during each dose may be correlated with the amount of drug required to address particularly high or low infestation patterns. Thus, for example, the amount of drug provided by a dose may be increased or subsequent doses may be delivered more frequently during periods, such as spring or summer, when parasitic infestations may be particularly common, and decreased to a level slightly above the efficacy threshold during fall and winter or other periods when parasite infestations are not as common.

In accordance with still yet another aspect of the invention, a plurality of different drugs may be automatically dosed during different periods. For example, concerns may be present about the use of two drugs because of their proclivity to interact and produce undesirable side effects. With the method of the present invention, a first drug may be delivered and allowed to fall below levels at which it is likely to interact with the second drug. The second drug may then be administered and allowed to fall to a sufficiently low level before the first drug is reintroduced. Thus, one can ensure that an animal has its medication administered at appropriate times without requiring one to be present each time one of the drugs is administered. Accurate, precise delivery of complex dosing regimens is thus achieved in an unattended and automatic fashion.

The dispensing apparatus is sufficiently small that it may be located within a collar or other device secured to the animal, If necessary, the dosages provided by the dispensing apparatus may be maintained within a single container for each dose, or larger doses may be achieved by using multiple containers.

Still yet another aspect of the present invention is mixing two or more drugs within a container or reservoir, or during application to achieve a desired balance of the two drugs which is available to the animal. The two drugs disposed in a single reservoir may be selected to interact with each other, or may be simply selected on the basis that dosing of the two drugs is desirable at approximately the same time. When dispensed from separate reservoirs, the drugs will typically interact in a symbiotic manner to further improve the efficacy of the drugs.

BRIEF DESCRIPTION OF THE DRAWINGS

The above and other objects, features and advantages of the invention will become apparent from a consideration of the following detailed description presented in connection with the accompanying drawings in which:

FIGS. 5A–5lD illustrate views of four preferred embodiments of a dispenser in accordance with the present invention;

DETAILED DESCRIPTION

Reference will now be made to the drawings in which the various aspects of the present invention will be described so as to enable one skilled in the art to make and use the invention. It is to be understood that the following description is only exemplary of the principles of the present invention, and should not be viewed as narrowing the pending claims.

Figure 2:
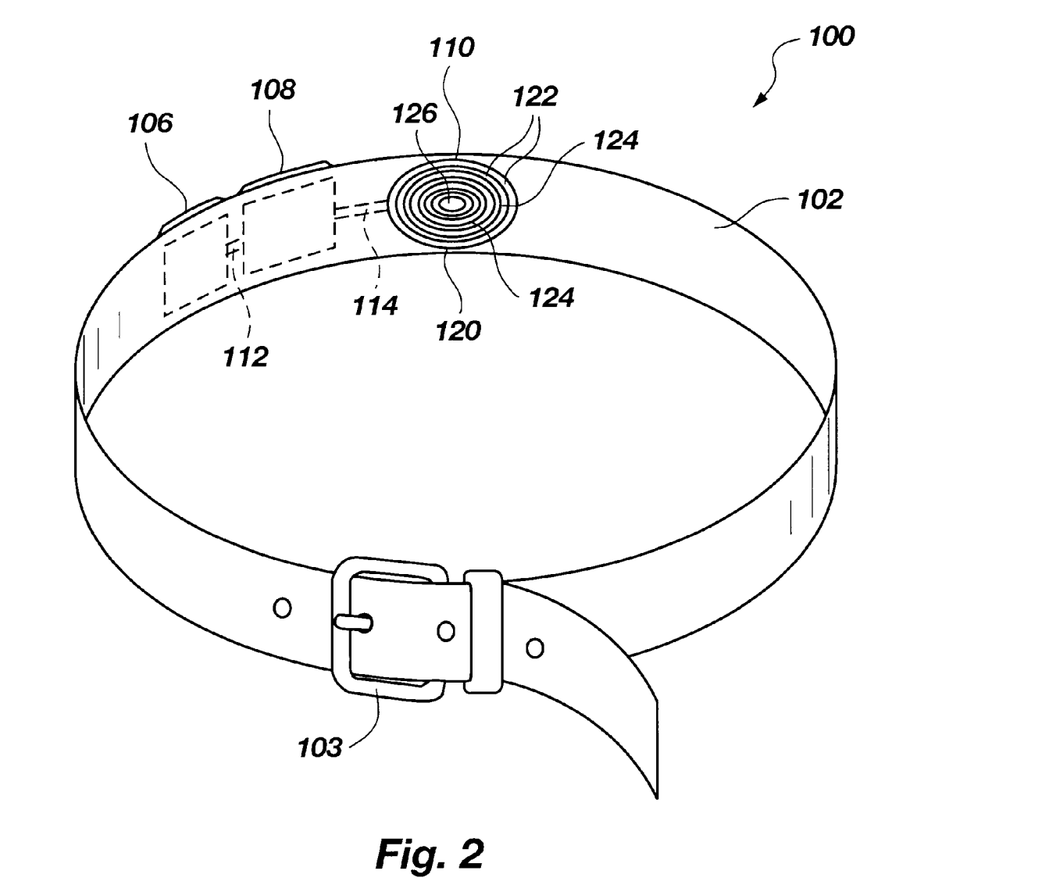
FIG. 2 shows a perspective view of a first embodiment of a drug delivery system in accordance with the present invention.

Referring to FIG. 2, there is shown a drug delivery system, generally indicated at 100, which may be used to practice the teachings of the present invention. The drug delivery system 100 includes a support structure, in this preferred embodiment a strap 102 in the form of a collar having a drug container or reservoir 106, a drug delivery device, such as a pump 108, and a dispenser 110 secured thereto. The strap 102 includes a conventional buckle-type fastener 103 but could include other suitable connecting devices known in the art. The reservoir 106 and pump 108 are in fluid communication with one another such that activation of the pump 108 draws a drug or drugs contained in the reservoir 106 from the reservoir 106, through the tubing 112, and into an inlet of the pump 108. The pump 108 then pumps the drug or drugs through an outlet, into the tubing 114, and to the dispenser 110.

The dispenser 110 illustrated with respect to FIG. 2 is comprised of a disc-like structure having a contact surface 120 defined by a plurality of substantially concentric raised portions or peaks 122 defining a plurality of lower portions or grooves 124. Proximate the center of the dispenser 110 is an opening or port 126 through which a drug or drugs supplied by the pump 108 are dispensed. The irregular configuration of the contact surface 120 of the dispenser 110 not only increases the surface area of the dispenser to be contacted by an animal wearing the collar 102, but holds the drug or drugs within the grooves 124 by capillary action until contacted by the animal wearing the collar 102.

Figure 3:
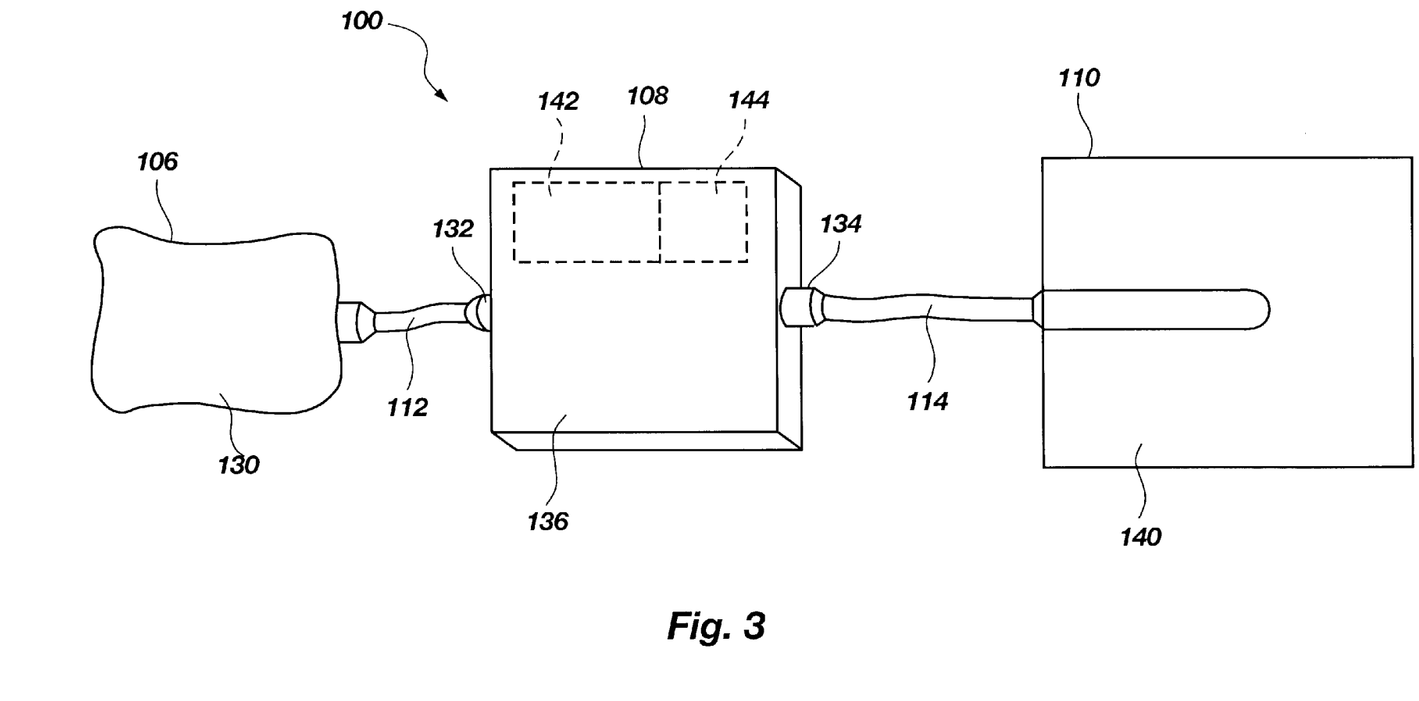
FIG. 3 shows a perspective view of the drug delivery system illustrated in FIG. 2.

Referring to FIG. 3, as viewed from the back side, the drug delivery system 100 includes a reservoir 106 that may comprise a flexible bag 130, such as of the type used for IV's in hospital and veterinary situations. The pump 108 includes an inlet port 132 for drawing a drug from the bag 130 through the tubing 112 and into the pump 108. The drug is then transferred from the pump 108, through an outlet port 134, through the tubing 114, and into the dispenser 110. It is contemplated that the reservoir 106 and pump 108 may be housed within the same unit such that the reservoir 106 would be fitted within the housing 136 of the pump 108. Likewise, the pump 108, and thus the reservoir 106, could be mounted directly on the back 140 of the dispenser 140 such that the reservoir 106, pump 108, and dispenser 110 form a single integrated unit that is secured to a support structure such as the collar 102 illustrated in FIG. 2. Preferably, however, the reservoir 106, pump 108, and dispenser 110 are of relatively thin construction as to cause minimal interference with movement or activity of the animal wearing the drug delivery system 100 and thus will be less likely to become damaged during use.

The pump 108 may include a controller 142, such as a microprocessor, that can be programmed to deliver the drug from the reservoir 106 to the dispenser 110 according to a preprogrammed dosing regimen. The dosing regimen may vary depending on the drug being adminstered, the size of the animal to which the drug is to be administered, the season, or other factors that may affect the desired dose. Accordingly, the pump 108 will deliver the drug to the dispenser 110 as commanded by the controller 142. Of course it may be necessary to provide battery or some other form of power to the pump 108 and controller 142.

It is also contemplated that the pump 108, and more specifically the controller 142, include a transmitter/receiver 144 in communication with the controller 142. Signals sent to and received by the transmitter/receiver 144 can either activate the pump 136 to begin pumping at a certain rate, may be employed to reprogram the dosing regimen, or both. Thus, as conditions change, such as when a particular parasite becomes more active, the drug delivery system 100 can be reprogrammed to increase the dosing regimen to counteract the increase in parasite population. Likewise, when the season changes and a particular parasite becomes dormant or substantially less active, the dosing regimen can be remotely altered to match the parasitic threat. This may be especially useful in farm situations where hundreds or thousands of animals are equipped with the drug delivery system 100 of the present invention. Thus, the amount of pesticide could be remotely adjusted for numerous animals without having to individually vary the dosing regimen on each animal.

Figure 4:
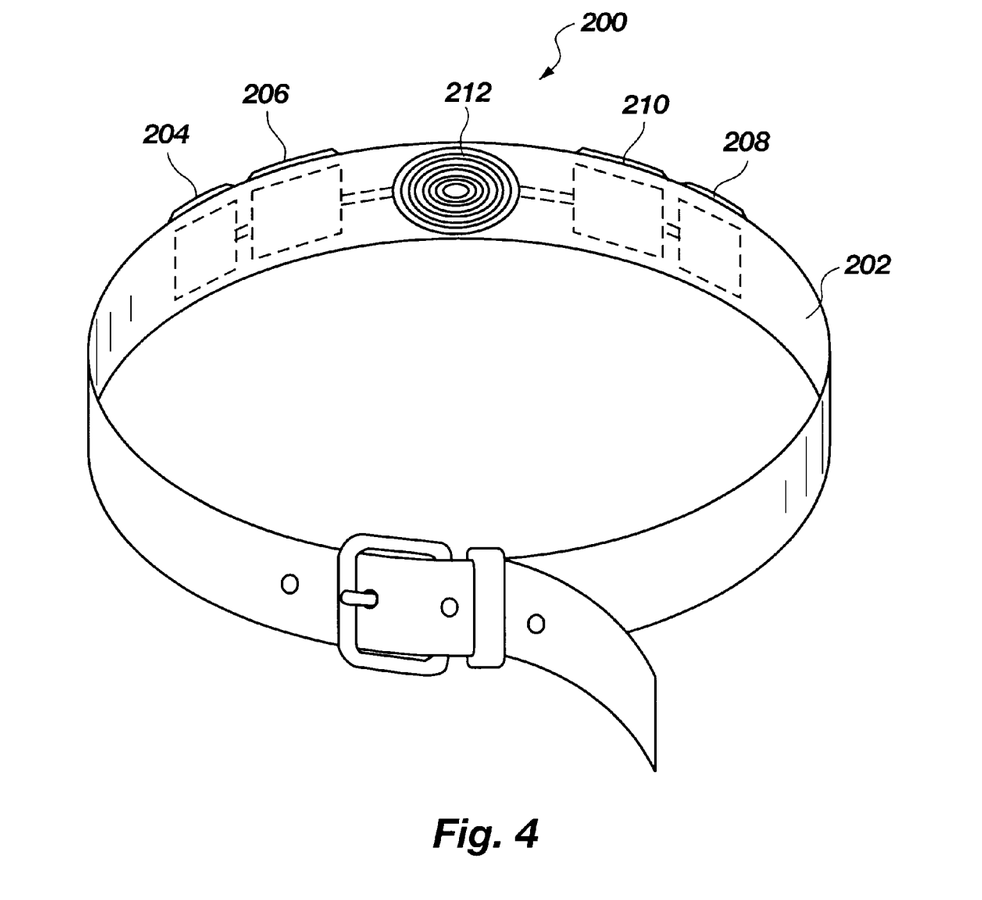
FIG. 4 shows a perspective view of a second preferred embodiment of a drug delivery system in accordance with the present invention.

As illustrated in FIG. 4, it is also contemplated that a drug delivery system 200 in accordance with the present invention may be configured to deliver more than one drug or one combination of drugs to an animal wearing the collar 202. In the preferred embodiment illustrated in FIG. 4, the drug delivery system 200 comprises a first reservoir 204 in fluid communication with a first pump 206 and a second reservoir 208 in fluid communication with a second pump 210. Each of the first and second pumps 206 and 210, respectively, are in fluid communication with a dispenser 212. Accordingly, each pump 206 and 210 can independently deliver their respective drug or combination of drugs to the dispenser 212. This may be especially beneficial where it is not desirable to substantially mix the drugs to be dispensed or where it is desirable to dispense the two drugs at different times. While FIG. 4 illustrates the drug delivery system having two pumps 206 and 210, it is equally contemplated that a single pump connected to two reservoirs could independently dispense drugs from the two reservoirs with the appropriate valving arrangement and logic, such as a microprocessor, to control actuation of such valves.

Figure 5A:
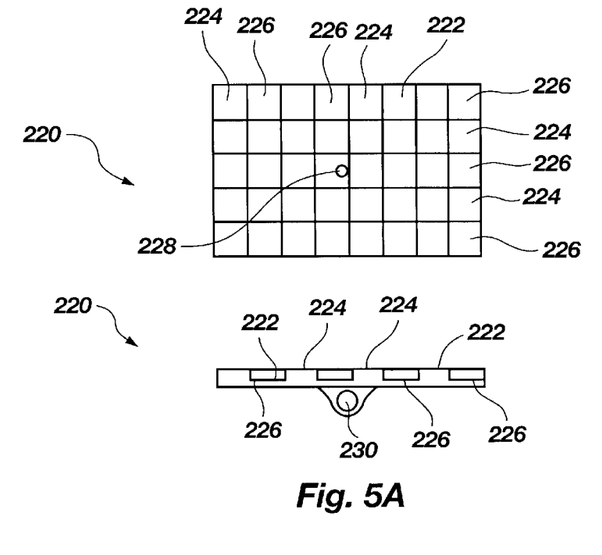

FIGS. 5A–5D illustrate several preferred embodiments of a dispenser in accordance with the present invention. FIG. 5A illustrates a front and side view of a dispenser, generally indicated at 220, having a front or contact surface 222 comprised of a plurality of raised portions 224 defining a plurality of lowered portions 226 in a checkerboard arrangement. Proximate the center of the contact surface 222, a drug dispensing port 228 is provided and is in communication with a tube attachment port 230 for attachment to a pump. The surface size of the raised and lowered portions 224 and 226, respectively, are for illustration purposes, and may be made much smaller to further increase the surface area of the dispenser 220 and the capillary action in each of the lowered portions 226.

Figure 5B:
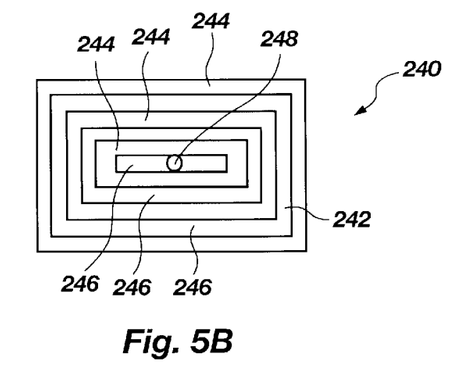

FIG. 5B illustrates another preferred embodiment of a dispenser 240 in accordance with the present invention in which the contact surface 242 of the dispenser 240 is comprised of a plurality of raised walls 244 defining a plurality of grooves 246 thereinbetween. A dispensing port or orifice 248 is provided proximate the center of the dispenser 240. Accordingly, as a drug is dispensed through the orifice 248, the drug will travel over the walls 244 and through the grooves 242, thus increasing the likelihood that the drug will be contacted by and delivered to the animal.

Figure 5C:
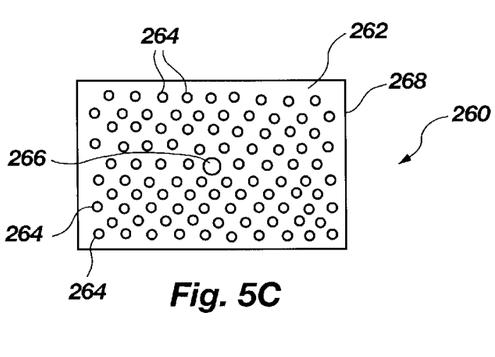

FIG. 5C illustrates yet another preferred embodiment of a dispenser, generally indicated at 260, in which the contact surface 262 includes a plurality of projections or nubs 264 extending therefrom. A dispensing port 266 is provided proximate the center of the dispenser 260. Accordingly, a drug dispensed through the dispensing port 266 must at least flow over and around a plurality of the nubs 264 before reaching a perimeter 268 of the dispenser 260, thus increasing the likelihood that the drug will be contacted and absorbed by the animal.

Figure 5D:
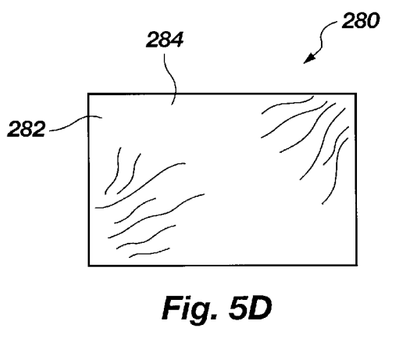

While the dispensing structures provided with reference to FIGS. 2, 5A, 5B, and 5C are preferably comprised of a substantially self supporting material such as a plastic or rubber-like compound, the dispenser 280 illustrated in FIG. 5D is comprised of a fabric or sponge-like material 282 defining the contact surface 284 of the dispenser 280. Accordingly, a drug or combination of drugs dispensed into the sponge-like material 282 will be held therein until the drug either dries within the sponge-like material or is deposited on the animal. Thus, there is little likelihood that the drug will drip or otherwise run from the dispenser 280, assuming that the pump associated therewith is controlled so that an excessive amount of drug is not delivered to the dispenser at any given time.

While, the present invention has been described in reference to several illustrated embodiments, it is contemplated that other dispenser configurations may work equally as well without departing from the spirit and scope of the present invention. It is also contemplated that various features of the illustrated dispenser embodiments may be combined. For example, the dispensers illustrated in FIGS. 5A, 5B, and 5C may be provided with a perimeter portion comprised of the fabric or sponge-like material illustrated with reference to FIG. 5D. In addition, it may be desirable to position the dispenser port at some location offset from the center of the dispenser in order to counteract gravitational affects on the dispensed drug.

Figure 6:
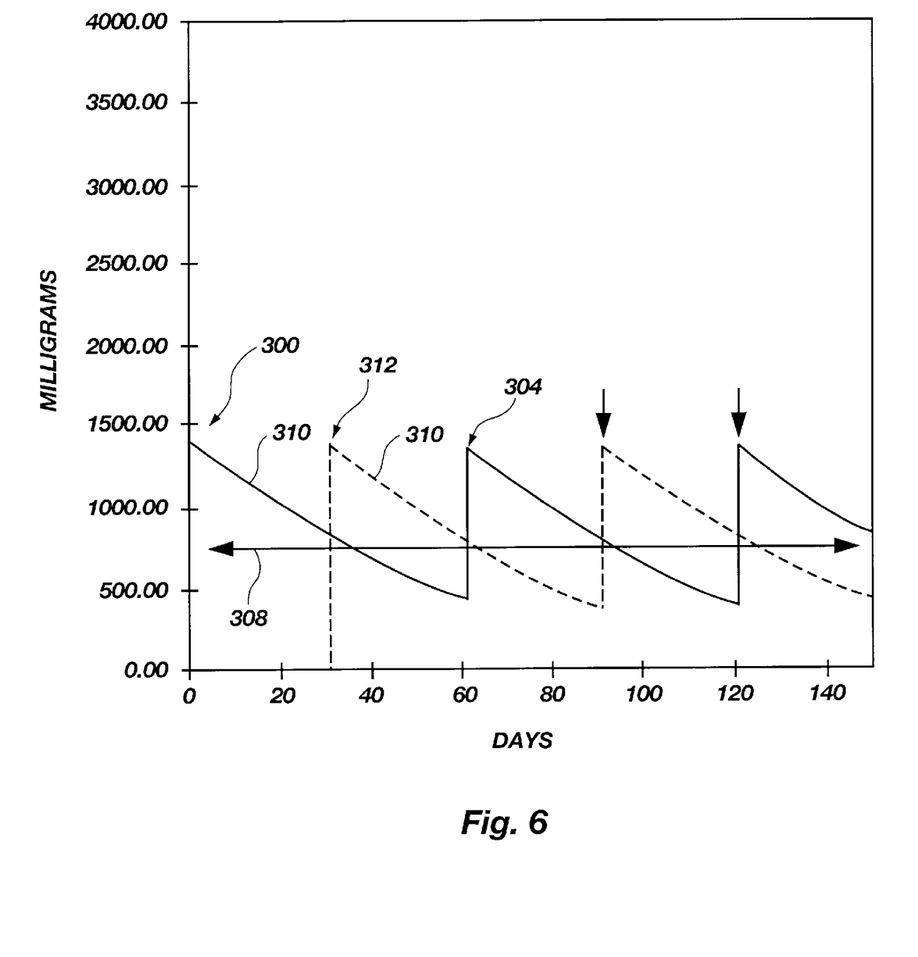
FIG. 6 shows a graph demonstrating a method of repetitive, alternating dosing in accordance with the principles of the present invention, along with a first-order kinetic decline for the delivery of each dose.

Referring now to FIG. 6, there is shown a graph demonstrating a method of dosing in accordance with the principles of the present invention, along with a first-order kinetic decline after delivery of each dose. For illustration purposes, the drug amounts required to kill flies is graphed.

An initial dose 300 of a first drug, represented by solid line 304, is provided to kill flies. As shown in FIG. 6, the initial dose is about 1400 milligrams. However, those skilled in the art will appreciate that the amount provided will depend both on the drug used, the type and size of the animal, and the disease. For illustration purposes, treatment of a parasitic fly infestation will be discussed, as those skilled in the art will be familiar with numerous parasiticides which may be used for such a purpose. After approximately 30 days, the levels of the first parasiticide 304 drop to near the efficacy threshold. Rather than providing additional quantities of the first drug 304, the drug delivery system (FIG. 2) is programmed to activate expulsion of a second drug 310 to provide the dosage indicated at 312. As shown in FIG. 6, 1400 milligrams of the second drug are provided to kill any parasites which have not been killed by the first drug 304.

As the second drug 310 falls toward the efficacy threshold 308, a sufficient quantity of the first drug 304 is again provided by the microdelivery system to bring the levels of the first drug 304 back up to 1400 milligrams. The amount of the first drug 304 necessary to reach the target dose is less than needed for the initial dose because of the residue first drug from the first dose. Thus, the second and subsequent dosings of either drug can typically be in smaller quantities, or delayed a sufficient period of time to prevent drug build up to levels which risk host toxicity. As shown in FIG. 6, approximately 900 milligrams is used for each dose after the initial dose for each drug.

By cycling the drugs in the manner described, considerable advantages are achieved. Of primary importance is that the cycling prevents the development of resistance to the parasiticide in the targeted parasite. There is always at least one of the drugs which is sufficiently above the efficacy threshold to eliminate the parasitic infestation. The two cycling drugs prevent multigenerational parasite turnover in the presence of subtherapeutic drug levels which is typically associated with development of resistance to drugs. Thus, resistance is substantially eliminated.

An additional advantage of the cycling is that the repetitive replenishment of drug keeps the total drug exposure for the host to a minimum. As shown in FIG. 6, one device administration has provided effective treatment of the animal for approximately five months. To achieve a similar treatment pattern with conventional dosage forms such as prior art diffusion devices would require the farmer, rancher, etc., to round up and treat the animal with the first or second drugs during each of the five months or periodically reapply diffusion-type devices. When dealing with large numbers of animals, the time and expense involved with such procedures is prohibitive.

Figure 7:
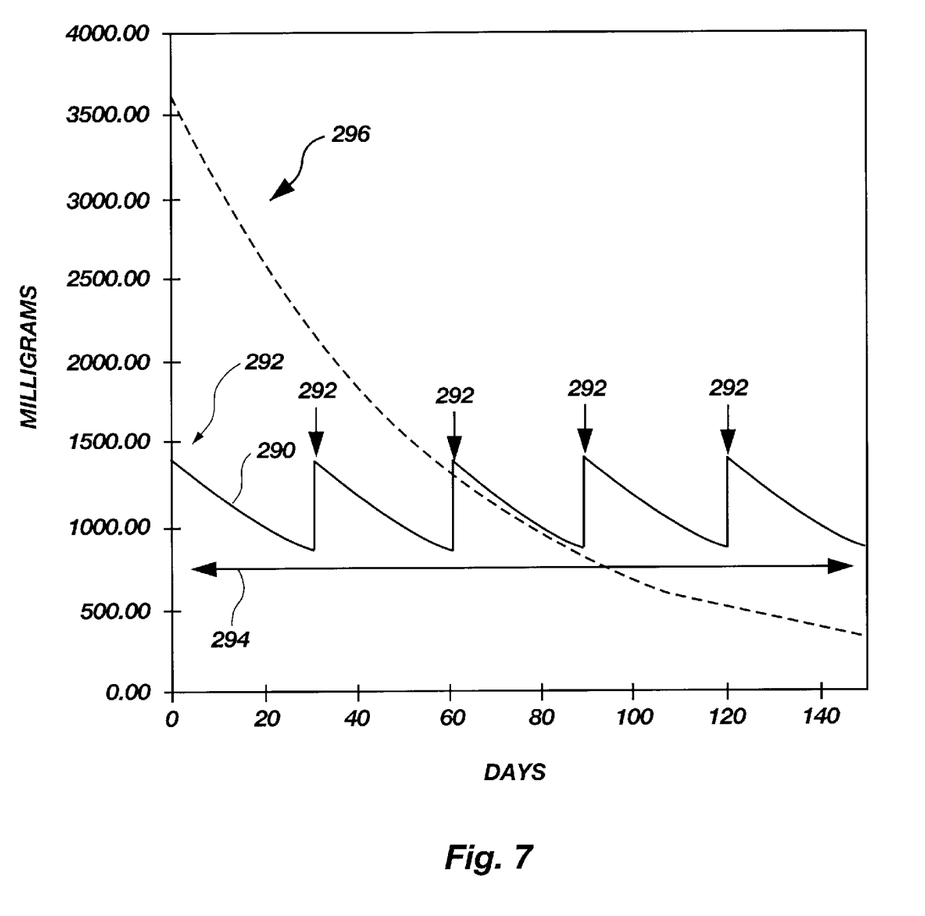
FIG. 7 shows a graph demonstrating a method of repetitive dosing in accordance with the principles of the present invention, along with a first-order kinetic decline for the delivery of each dose.

While FIG. 6 illustrates a method of dosing in which dosing of two drugs is alternated in order to maintain the efficacy of at least one of the drugs at any given time, FIG. 7 illustrates a similar method of dosing using a single drug, illustrated by line 290, that is pulsed, indicated at 292, in order to stay above the efficacy threshold, indicated by line 294, of the drug 290. In comparison to a diffusion controlled mechanism, illustrated by dashed line 296, that results initially in very high drug levels that continually decline until efficacy is lost, when dosed in a pulsatile fashion, the drug 290 is replenished on the delivery system before the subtherapeutic levels are achieved. Preferably, the duration of the dosing activity is readily controlled to provide coverage over the entire parasite season.

Preferably, the dosing pattern can continue for a predetermined period of time, such as for 6 months. The actual time during which the delivery system will typically be used depends on the parasite infestation patterns and the amount of the drug or drugs which may be held in the delivery system.

While the graph of FIG. 6 shows the first and second drugs alternatingly falling below their efficacy thresholds, those skilled in the art will appreciate that a desirable dosing pattern is to keep both drugs above their efficacy thresholds for the entire period of treatment. Thus, instead of alternating the first and second drugs on a monthly basis, dosing may occur on a biweekly basis or a larger dose may be supplied. Such a dose, however, will be well below the potentially dangerous doses which attend administration of diffusion-type devices.

EXAMPLE 1

In accordance with the graph of FIG. 6, permethrin and chlorpyrifos insecticides are disposed in the delivery system 200 of FIG. 4 for control of ectoparasites such as horn flies. The insecticides are formulated in combination with solvents, polymers and other additives as necessary to retard depletion of an expelled dose over a one-month period. A first dose of permethrin is supplied in sufficient quantity to raise the amount of available permethrin above the efficacy threshold. Applying a first-order kinetic depletion curve to the amount of permethrin that is available, the permethrin is formulated to stay above the efficacy threshold for one month. Similarly, the delivery system 100 is programmed to release a sufficient quantity of chorpyrifos to bring the level of the drug above the efficacy threshold for chlorpyrifos and maintain a level above the efficacy threshold for one month. The delivery system 100 actuates a compartment holding the largest dose of chlorpyrifos four weeks after the first dose of permethrin is released.

Four weeks after the first dose of chlorpyrifos is released, the delivery system again actuates a compartment containing permethrin to release additional quantities of that drug. Because of the residual quantity of permethrin from the initial permetrin dose, the second permethrin dose will be a fraction of the first permethrin dose. According to FIG. 6, the second permetrin dose would be approximately 65% of the initial permethrin dose. Therefore, the delivery system will be programmed as to which individual compartment to release for the first and all subsequent doses.

By continuing to alternate doses of the first and second drugs, the delivery system 200 provides doses which prevent parasite infestations for approximately six months. This is accomplished with a single device administration, saving the farmer or rancher time and money, while allowing both drugs to be kept well below levels which might induce host toxicity. Additionally, tolerance development by the parasites is nearly eliminated because the continual replenishment and alternating of the pesticides precludes multigenerational parasite turnover under conditions of sub-lethal insecticide exposure that is required for tolerance to develop. It is important to recognize in accordance with the present invention that alternating, as used herein, may include a one to one sequence, e.g. A-B-A-B . . ., or some other combination, e.g. A-A-B-A-A-B-A-B-B . . ., as may be desired to most efficaciously minimize the threat of parasite, etc., infestation during a predetermined period of time, while minimizing the risk of toxicity to the animal.

Figure 8:
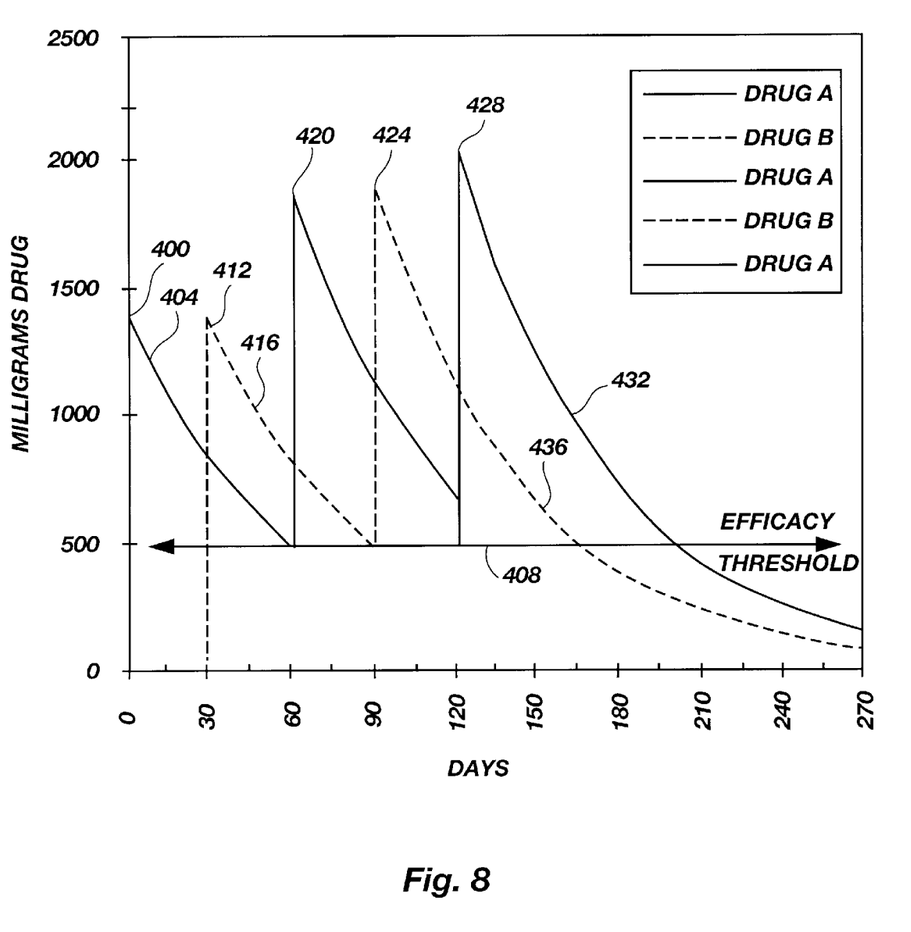
FIG. 8 shows a graph of another dosing procedure in accordance with the present invention.

Referring now to FIG. 8, there is shown a graph of another dosing procedure in accordance with the present invention. An initial first dose 400 is provided of a first drug, the level of which is indicated by line 404. The initial first dose 400 of the first drug is approximately 1400 milligrams. At such a quantity, the amount of the first drug on the animal or available on a device configuration such as an ear tag, remains above the efficacy level 408 for approximately 60 days.

Approximately one month after the first drug is released, an initial dose 412 of a second drug, indicated by the dashed line 416, is released. The amount of the second drug 416 which is released is also 1400 milligrams and will take approximately 60 days to drop below the efficacy threshold for the second drug. For ease of reference, the efficacy threshold for the second drug is indicated as being the same as the efficacy threshold 408 for the first drug. Those skilled in the art will appreciate that the efficacy threshold for each drug used must be considered when determining the quantity of that drug released and the time between dosing and the presence of subtherapeutic levels of the drug.

Unlike the dosing regimen in FIG. 6, the amount of drug delivered with each dose is kept the same. Thus, because the level of the first drug has fallen to 500 milligrams, providing a second dose of 1400 milligrams, as indicated at 420, results in 1900 milligrams of therapeutically available drug. Likewise, a similar increase in the level of the second drug is achieved by use of a full 1400 milligram dose of the second drug, indicated at 424.

FIG. 8 also shows a third dose, indicated at 428, of the first drug. The third dose 428 is also 1400 milligrams, thereby bringing the amount of the first drug to a peak of slightly more than 2000 milligrams. Each of the two drugs are eliminated or degraded with a first-order kinetic decline, as indicated at 432 for the first drug and 436 for the second drug.

The dosing of the drugs so as to create an increase in the drug level in the animal with each subsequent dose can be used advantageously. Rather than requiring the delivery system 100 or 200 to be programmed to release a first (higher) dose of each drug, the system must only ensure that the same amount of drug is released at each pulse. To prevent build-up of the drug or drugs, all doses after the second dose for each drug would simply be delayed.

In the alternative, the escalating quantity achieved by the dosing level as shown in FIG. 8 can be used to improve the correlation between dosing and infestation patterns. For example, if a particular parasite infestation is most common during a specific month or period, the delivery system can be programmed to release a compartment containing a particularly high quantity of one or both drugs during the infestation period. Doses subsequent to the infestation period would be modified to return the drugs to a level desired when high-level infestation is not a concern.

Of course, a single drug could be used in the dosing pattern. As will be apparent to those skilled in the art from FIG. 8, either of the drugs delivered could be administered periodically to keep the drug doses to a minimum while ensuring that the available amount of the drug remains above the efficacy threshold. In such a manner, the development of resistance would be greatly diminished, as the available amount of the drug remains above the subtherapeutic level needed for resistance to develop.

The use and application of a delivery system, such as the drug delivery systems illustrated in FIGS. 2, 3, and 4, include the use of a pump or some other device that can transport a drug contained in a reservoir to a dispenser in accordance with the present invention. Accordingly, a pump, such as the pump disclosed in U.S. Pat. No. 5,603,354, herein incorporated by reference, may be employed for the long-term, unattended topical delivery of parasiticides for the control of ectoparasites.

Figure 9:
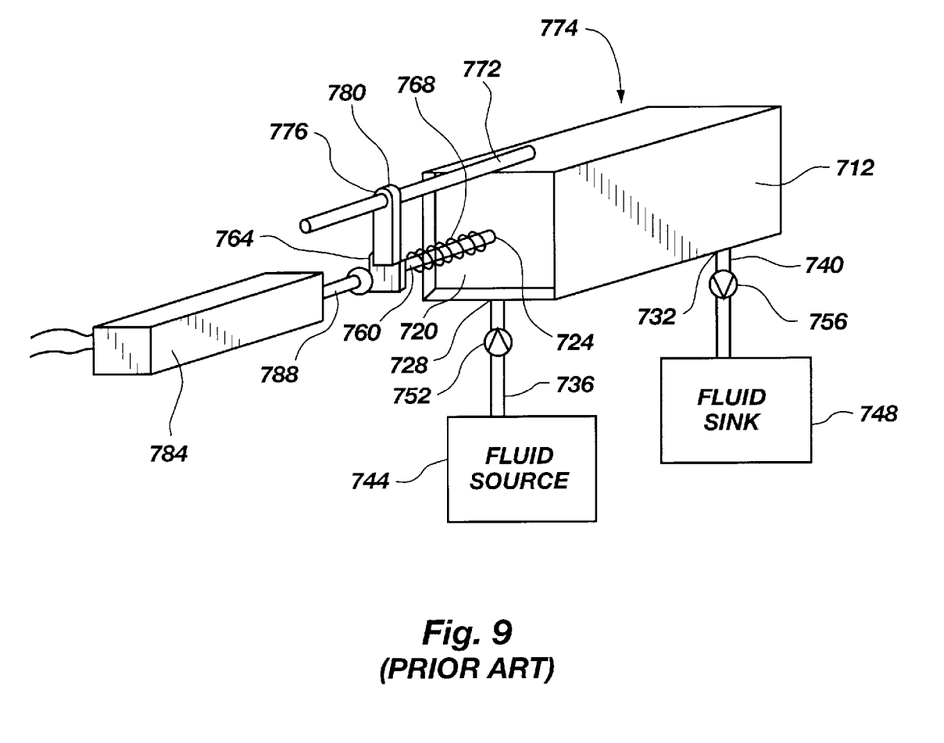
FIG. 9 is a perspective view of a pump which may be used with the drug delivery system in accordance with the present invention.

FIG. 9 illustrates a perspective view of a volummetric pump disclosed in U.S. Pat. No. 5,603,354 and includes a generally elongate housing 774, formed with an elongate city therein. The housing 774 might illustratively be formed with an exterior shell 712 made of metal or hard plastic, and an interior filler disposed against the shell 712, with the cavity formed centrally therein. The filler could similarly be metal or hard plastic.

Disposed in one end of the housing 774 is a resilient sheet of material 720 made, for example, of latex rubber, silicone rubber, or nitride rubber. The sheet of material 720 fills the end of the housing 774 to prevent commununication between the outside of the housing and the cavity except through an aperture 724 positioned in line with the cavity.

An inlet duct 728 is formed in the housing 774 generally adjacent to the sheet of material 720, to communicate with the cavity, and an outlet duct 732 is similarly formed in the housing to communicate with the cavity at the other end thereof. Conduits 736 and 740 respectively couple ducts 728 and 732 to a fluid source 744, such as a reservoir or container, and a fluid sink 748, such as a dispenser. Check valves 752 and 756 are disposed respectively in conduits 736 and 740 to allow fluid to flow from the fluid source 744 into the cavity and prevent the reverse flow, and to allow fluids to flow from the cavity to the fluid sink 748 and prevent the reverse flow. The fluid source 744 could be any source of fluid which it is desired be pumped to fluid sink 748, such as an IV administration set which includes a bottle of fluid to be administered to a patient, with the fluid source 744 being the bottle and the fluid sink 748 being the patient receiving the fluid. Of course, as will be evident upon further discussion, the fluidic pump could be used in a variety of environments.

An elongate shaft or plunger 760 is disposed in the aperture 724 of the sheet of material 720 to extend at least partially into the cavity of the housing 774. The shaft 760 may have a circular cross section and have a somewhat smaller circumference than that of the cavity so that the shaft may be moved in a reciprocating fashion back and forth in the aperture 724 and cavity. The aperture 724 is preferably shaped similarly to the cross-sectional shape of the shaft 760 and is preferably the same or slightly smaller in size in order to completely surround and grip the shaft to form a sphincter seal and prevent fluid from escaping the cavity. As the aperture is formed in the resilient sheet of material 720, the aperture conforms to the shape of the shaft 760 even if their shapes are not identical, though it will be obvious to those skilled in the art that the more shapes differ the less effective the seal will be.

Disposed on the free end of the shaft 760 is a bumper pad 764. A coil spring 768 is disposed about that portion of the shaft 760 which is outside of the housing to provide a bias force against the bumper pad 764 to urge the shaft outwardly from the housing.

A support rod 772 is mounted on the top of the housing 774 and extends forwardly therefrom, and a stopper finger 776 is slidably mounted on the rod 772 so that it may be slid forwardly or rearwardly along the rod. A set screw 780 is provided in the stopper finger 776 to allow for setting or fixing the position of the stopper finger on the rod. Stopper finger 776 extends downwardly to a position in the pathway of possible movement of the bumper pad 764 to prevent the bumper pad and thus the shaft 760 from moving outwardly from the housing 774 beyond the location of the stopper finger. The bumper pad 764 rests against the lower end of the stopper finger 776 to illustrate that the bumper pad 764 and shaft 760 are prevented from moving any further outwardly from the housing 774. The setting of the stopper finger 776 by means of the set screw 780 determines the stroke or excursion of movement of the shaft 760 within the cavity of the housing 774.

A driving mechanism 784, such as a solenoid, is positioned in front of the housing 774 so that a solenoid drive core 788 extends toward the bumper pad 764 as shown. When the drive mechanism 784 is activated (for example by applying an electrical current to a solenoid), the driver core 788 is caused to move towards the bumper pad 765, engage it and move the bumper pad and the shaft 760 toward the housing 774 so that the shaft moves further into the cavity of the housing. When the drive mechanism 784 is deactivated, the drive core 788 retracts into the drive mechanism 784 allowing the coil spring 768 to urge the bumper pad 764 and thus the shaft 760 outwardly from the housing pad 764 until the bumper pad contacts the stopper finger 776. Alternative activation and deactivation of the drive mechanism 784 will thus result in the shaft 760 being reciprocated within the cavity of the housing 774.

In operation, when the shaft 760 is moved further into the cavity, any fluid within the cavity is forced into the conduit 740 and through the check valve 756 to the fluid sink 748. When the shaft is allowed to retract or move outwardly of the cavity, a negative pressure is created in the cavity, causing fluid to be drawn from the fluid source 744 through the check valve 752 and into the cavity. The continued reciprocation of the shaft 760 thereby provides for pumping fluids from the fluid source 744 to the fluid sink 748.

Other delivery systems may also be employed to administer drugs in a manner in accordance with the method of the present invention. For example, the pressure-driven attachable topical fluid delivery system disclosed in U.S. Pat. No. 5,618,269 and the piston-actuated attachable topical fluid delivery system described in U.S. application Ser. No. 08/434,463 both to Jacobsen et al. may be employed to deliver the drug(s) in accordance with the present invention.

EXAMPLE 2

In this example, the delivery system, such as the drug delivery system 100 illustrated in FIG. 2, automatically delivers a maintenance dose of 10 to 200 microliters per day of the ectoparasiticide permethrin, formulated as a 60% w/w solution in methyl carbitol or other solvent, onto the fur and skin of dogs or cats. The microliters delivered per day are determined by the size of the animal and the susceptibility of the parasites in question. In most cases fleas and ticks are the target parasites. The maintenance dose is selected to provide high level parasite control with a minimum amount of parasiticide. On a previously untreated animal, it is frequently desirable and advantageous to provide an initial loading dose on the first day of treatment. Loading doses typically vary between 100 and 1500 microliters. The loading dose rapidly raises the parasiticide level on the host animal into the lethal range, thus providing rapid kill of the offending parasite(s) and providing rapid relief to the host animal. The maintenance dose then maintains sufficient levels of the parasiticide to control the infestation at an acceptable level (>80% efficacy is typically desired) for a prolonged period of several weeks up to one year. Sufficient drug for the loading dose and all maintenance doses is contained within a reservoir container from which the delivery system dispenses the programmed doses.

EXAMPLE 3

In this example, a drug delivery system, such as the drug delivery system illustrated in FIG. 2, dispenses parasiticides for the control of both ectoparasites and endoparasites. In this preferred embodiment, the parasiticide is a combination of permethrin and ivermectin dissolved in an appropriate solvent such as methyl carbitol, Dowanol, or hexylene glycol. The permethrin is present at a 60% w/w concentration and the ivermectin at a 1% w/w concentration. The combination formulation is dosed as disclosed in Example 2, however, the spectrum of target parasites is expanded to include both ectoparasites (e.g., fleas and ticks) and endoparasites such as the tissue stage of *Dirofilaria immitis* larvae which is ultimately responsible for lethal heartworm disease. Although some susceptible types of gastrointestinal worms would also be controlled by this formulation, improved control of gastrointestinal worms (e.g., hookworms, roundworms, and whipworms) would be achieved by substituting milbemycin oxime for the ivermectin. Due to the exquisite sensitivity of *Dirofilaria. immitis* to the avermectin and milbemycin classes of parasiticides, 100% control of *Dirofilaria immitis* is achieved. The drug delivery system relieves the animal handler from frequent manual dosing and assures that doses are given at the proper time and in the proper amount. This provides for uninterrupted drug coverage for the animal and eliminates the possibilities for parasite infestation that inevitably accompany human errors in manually administering frequent, and repetitive doses.

In accordance with the present invention, it is desirable that all components be sufficiently inexpensive to be disposable, including the pump, if desired. Thus, the animal handler gains complete flexibility in the use of both the drug and the delivery device to best meet the individual needs of each animal.

Those skilled in the art will appreciate that regardless of which delivery system is used, the animal handler responsible for assuring that drug therapy is provided can utilize established pharmacokinetic/pharmacodynamic principles and program the devices to deliver an optimal dosing regimen. Relying on this information, the programmer can determine not only when a drug should be released, he or she can selectively control the selected delivery system to provide different dosing levels to select an optimum dosing pattern for the particular use.

While the present invention will be desirable for a large number of insecticides, parasiticides and other drugs as listed in the Merck Index, the following drugs are currently viewed as being highly desirable for administration in accordance with the principles of the present invention which are set forth above:

chlorpyrifos
diazinon
permethrin
lambdacyhalofthrin
pyrimiphos methyl
ivermectin
doramectin
moxidectin and
insect growth regulators Thus there is disclosed an apparatus for automatic dosing of one or more drugs. Those skilled in the art will recognize numerous modifications which can be made without departing from the scope and spirit of the invention. The appended claims are intended to cover the scope of the invention.

What is claimed is:

1. An apparatus for the delivery of at least one drug to an animal, comprising:

a support structure securable to a body part of an animal;

a first reservoir secured to the support structure and containing at least one drug therein;

a first delivery device in fluid communication with the reservoir; and a topical dispenser comprising a pad having an irregular contact surface exposed on a side of the support structure to be in substantial contact with an animal wearing the support structure, said dispenser being in fluid communication with the delivery device, whereby activation of the at least one delivery device transfers the at least one drug from the reservoir to the dispenser.

2. The apparatus of claim 1, wherein the support structure comprises a collar with the reservoir, the delivery device, and the dispenser disposed thereon.

3. The apparatus of claim 1, wherein the irregular contact surface of the pad comprises a plurality of concentric ribs extending from a surface thereof and defining a plurality of grooves thereinbetween.

4. The apparatus of claim 3, wherein said delivery device is in fluid communication with a center portion of the pad for dispensing the at least one drug contained in the reservoir through the center portion of the pad.

5. The apparatus of claim 1, wherein the irregular contact surface of the pad comprises at least one of a plurality of walls defining a plurality of grooves thereinbetween, a plurality of raised portions defining a plurality of lowered portions, and a plurality of nubs.

6. The apparatus of claim 2, wherein the dispenser is substantially contained within the collar.

7. The apparatus of claim 1, further including a second reservoir and a second delivery device in fluid communication with the dispenser.

8. The apparatus of claim 7, wherein the second reservoir contains at least one other drug of different composition than the at least one drug contained in the first reservoir.

9. An apparatus for the delivery of at least one drug to an animal, comprising:

a collar mountable about a body portion of an animal;

a pump secured to said collar, said pump having an inlet and an outlet;

a drug reservoir in fluid communication with said inlet of said pump; and a dispensing device comprising a pad having an irregular contact surface exposed on a side of the support structure to be in substantial contact with said animal wearing the support structure, said dispenser being in fluid communication with said outlet of said pump.

10. A method of delivering at least one drug to an animal, comprising:

attaching a drug delivery system comprising a support structure securable to a body part of an animal, a first reservoir secured to the support structure and containing at least one drug therein, a first delivery device in fluid communication with the reservoir, and a topical dispensing pad having an irregular contact surface exposed on a side of the support structure to be in substantial contact with an animal wearing the support structure, said dispenser being in fluid communication with the delivery device and in at least partial contact with the animal;

programming the drug delivery system to dispense the at least one drug to the topical dispensing pad according to a desired dosing regimen;

actuating the drug delivery system to dispense doses of the at least one drug to the dispensing pad in accordance with the desired dosing regimen, each of said doses being of an amount that can be adequately contained within the topical dispensing pad.

11. The method of claim 10, wherein said doses are spaced an amount sufficient to adequately ensure that a prior dose has been sufficiently delivered to the animal.

12. The method of claim 10, further including at least one other drug, and said drug delivery system dispensing said at least one other drug to the topical dispensing pad.

13. The method of claim 10, wherein an initial dose is a loading dose of the at least one drug.

14. The method of claim 13, wherein subsequent doses are maintenance doses of an amount less than the initial dose.

15. The method of claim 10, wherein said at least one drug is selected from a parasiticide for the control of at least one of an ectoparasite and endoparasite.

16. The method of claim 15, wherein said at least one drug is selected from the group comprising permethrin and ivermectin.

17. The method of claim 10, wherein said at least one drug is selected from the group comprising antibiotics, antivirals, and antifungals.

18. The method of claim 10, wherein each of said doses are provided at preprogrammed intervals to ensure that a level of drug in the animal stays above an efficacy level of the at least one drug.

19. The method of claim 12, wherein a first dose of the at least one drug is dispensed to the topical dispensing pad and a first dose of the at least one other drug is dispensed to the topical dispensing pad at a first predetermined time after the first dose of the at least one drug.

20. The method of claim 19, wherein the method further comprises delivering additional doses of the at least one drug and the at least one other drug in an alternating fashion, each dose being spaced a predetermined period of time.

* * * * *